United States Patent [19]
Wehner et al.

[11] Patent Number: 6,063,981
[45] Date of Patent: May 16, 2000

[54] ADHESIVE FOR USE IN DISAPOSABLE ABSORBENT PRODUCTS

[75] Inventors: Jason K. Wehner; Thomas Kremer, both of Appleton, Wis.

[73] Assignee: Kimberly-Clark Worldwide, Inc., Neenah, Wis.

[21] Appl. No.: 09/009,111

[22] Filed: Jan. 20, 1998

[51] Int. Cl.$^7$ .................................................. A61F 13/15
[52] U.S. Cl. ...................... 604/367; 604/358; 604/365; 604/385.1
[58] Field of Search ................................. 604/367, 358, 604/365, 385.1

[56] References Cited

U.S. PATENT DOCUMENTS

| | | | |
|---|---|---|---|
| 3,896,069 | 7/1975 | Kosaka et al. | 260/28.5 |
| 4,705,812 | 11/1987 | Ito et al. | 521/92 |
| 5,455,111 | 10/1995 | Urey | 428/315.5 |
| 5,509,142 | 4/1996 | Connell et al. | 2/79 |
| 5,695,868 | 12/1997 | McCormack | 428/283 |
| 5,843,056 | 12/1998 | Good et al. | 604/367 |

FOREIGN PATENT DOCUMENTS

| | | |
|---|---|---|
| 0 296 787 A1 | 12/1988 | European Pat. Off. . |
| WO 97/33921 A1 | 9/1987 | WIPO . |
| WO 94/26834 A1 | 11/1994 | WIPO . |
| WO 97/04955 A1 | 2/1997 | WIPO . |
| WO 98/29246 A1 | 7/1998 | WIPO . |

OTHER PUBLICATIONS

American Society for Testing Materials (ASTM) Designation: D 36–86 (Reaaproved 1989), "Standard Test Method for Softening Point of Bitumen (Ring–and–Ball Apparatus)," pp. 9–12, published Apr. 1986.

American Society for Testing Materials (ASTM) Designation: D 3461–85 (Reapproved 1989), "Standard Test Method for Softening Point of Asphalt and Pitch (Mettler Cup–and–Ball Method)," pp. 225–230, published Jan. 1986.

American Society for Testing Materials (ASTM) Designation: D 4440–95a, "Standard Practice for Rheological Measurement of Polymer Melts Using Dynamic Mechanical Procedures," pp. 38–40, published Dec. 1995.

American Society for Testing Materials (ASTM) Designation: E 96–80, "Standard Test Methods for Water Vapor Transmission of Materials," pp. 742–751, published Feb. 1981.

"Elastomer Technology Handbook," edited by Nicholas P. Cheremisinoff, CRC Press, 1993, Chapter 24, pp. 835–856.

Patent Cooperation Treaty Search Report from the International Search Authority, International Application No. PCT/US 98/27737 dated Jun. 7, 1999.

*Primary Examiner*—John G. Weiss
*Assistant Examiner*—Miley Craig Peppers, III
*Attorney, Agent, or Firm*—Sebastian C. Pugliese, III

[57] ABSTRACT

Disclosed is the use of an adhesive to prepare a disposable absorbent product intended for the absorption of liquids such as body liquids. It is generally desired that the adhesive exhibits a storage modulus greater than about $1 \times 10^8$ dynes per square centimeter across the temperature range of about 0° F. to about 130° F. The use of such an adhesive results in a reduced visibility of the adhesive through the outer sheets, such as breathable films, of a disposable absorbent product to a wearer or user, thereby improving the aesthetics of the disposable absorbent product.

14 Claims, 1 Drawing Sheet

6,063,981

ADHESIVE FOR USE IN DISAPOSABLE ABSORBENT PRODUCTS

BACKGROUND OF THE INVENTION

1. Field of the Invention

The present invention relates to the use of an adhesive to prepare a disposable absorbent product intended for the absorption of liquids such as body liquids. The adhesive exhibits a reduced visibility through the outer sheets of the disposable absorbent product to a wearer or user, thereby improving the aesthetics of the disposable absorbent product.

2. Description of the Related Art

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These disposable absorbent products, when appropriate, usually include some type of fastening system for fitting the product onto the wearer. Adhesives, often referred to as construction adhesives, are generally used to join the different parts of the disposable absorbent product together.

For aesthetic reasons related to consumer acceptance, typical topsheet and backsheet materials are generally desired to appear opaque or white in color. One known method of achieving such opacity or whiteness of topsheet or backsheet material is to incorporate a pigment, such as titanium dioxide ($TiO_2$), into the formulation used to prepare the topsheet or backsheet material. However, the incorporation of such pigments is generally undesirable to the manufacturer due to the additional cost incurred by the use of such pigments.

Although current disposable absorbent products have been generally accepted by the public, these products still have need of improvement in specific areas. Backsheets often used in disposable absorbent products are generally prepared from liquid-impermeable materials which function to contain liquids, such as water, urine, menses, or blood, within the absorbent core of the disposable absorbent product and to protect a wearer's outer garments from soiling. However, such impermeable backsheets are sometimes perceived by the wearer as causing the disposable absorbent product to be hot and uncomfortable. Further, the impermeability of such backsheets generally precludes the self-drying of the disposable absorbent product which would otherwise occur because of evaporation of the liquids contained therein.

Breathable nonwoven materials have therefore been developed and employed in disposable absorbent products to improve the overall performance of such disposable absorbent products. Such breathable materials are generally impermeable to liquid but are permeable to vapor. Breathable backsheets generally provide a cooler disposable absorbent product and permit some self-drying of the disposable absorbent product while it is being worn. As indicated, such breathable backsheets are intended to allow for the passage of vapor through them while retarding the passage of liquid.

An example of a breathable material useful as a backsheet in a disposable absorbent product is a breathable film comprising a polyolefin resin, such as polypropylene or polyethylene, and an inorganic filler, such as calcium carbonate. When the film is stretched during processing, the inorganic filler generally causes a network of holes to be formed in the film. Such holes are generally small enough to prevent the passage of a liquid, but are generally large enough to allow vapor to pass through the holes. Such holes have also, in certain instances, been found to provide a secondary benefit of providing a whiteness or opacity to the film material by scattering light in the same manner as solid pigment particles, thereby eliminating the need for the use of pigments in the film material.

However, when such breathable films, not including any pigments, are attached to the other components in a disposable absorbent product by the use of typical construction adhesives, a problem sometimes referred to as adhesive staining is generally encountered, wherein the applied adhesive pattern, such as lines or swirls, is visible through the breathable film. Such adhesive staining is undesirable in that it generally negatively affects the aesthetics and consumer-perceived quality of the disposable absorbent product. Although such adhesive staining might be controlled by using pigments or a higher basis weight breathable film, the use of such pigments or higher basis weight film adds additional costs to the manufacturing of the disposable absorbent product.

As such, there is a need for adhesive materials that may be used in disposable absorbent products that allow for the use of nonwoven materials, such as breathable films, that don't include pigments while not negatively affecting the aesthetics and consumer-perceived quality of the disposable absorbent product.

It is therefore an object of the present invention to provide an adhesive, which exhibits unique rheological properties, which is suitable for use in preparing a disposable absorbent product.

It is also an object of the present invention to provide a disposable absorbent product comprising a nonwoven material, such as a breathable film, which exhibits desirable aesthetic properties.

It is also an object of the present invention to use an adhesive, which exhibits unique rheological properties, to prepare a disposable absorbent product which exhibits desirable aesthetic properties.

SUMMARY OF THE INVENTION

The present invention concerns an adhesive that is useful in preparing a disposable absorbent product. The adhesive exhibits a reduced visibility through the outer sheets of the disposable absorbent product to a wearer or user, thereby improving the aesthetics of the disposable absorbent product.

One aspect of the present invention concerns an adhesive that exhibits desirable rheological properties that are suitable for achieving desirable aesthetic properties in a disposable absorbent product.

One embodiment of such an adhesive is an adhesive that exhibits a storage modulus greater than about $1 \times 10^6$ dynes per square centimeter across the temperature range of about 0° F. to about 130° F.

In another aspect, the present invention concerns the use of an adhesive that exhibits a storage modulus greater than about $1 \times 10^6$ dynes per square centimeter across the temperature range of about 0° F. to about 130° F. to prepare a disposable absorbent product.

In another aspect, the present invention concerns a disposable absorbent product comprising a topsheet, a backsheet attached to the topsheet, an absorbent structure positioned between the topsheet and the backsheet, and an adhesive that exhibits desirable rheological properties that are suitable for achieving desirable aesthetic properties in the disposable absorbent product.

DETAILED DESCRIPTION OF THE PREFERRED EMBODIMENTS

Figure 1:
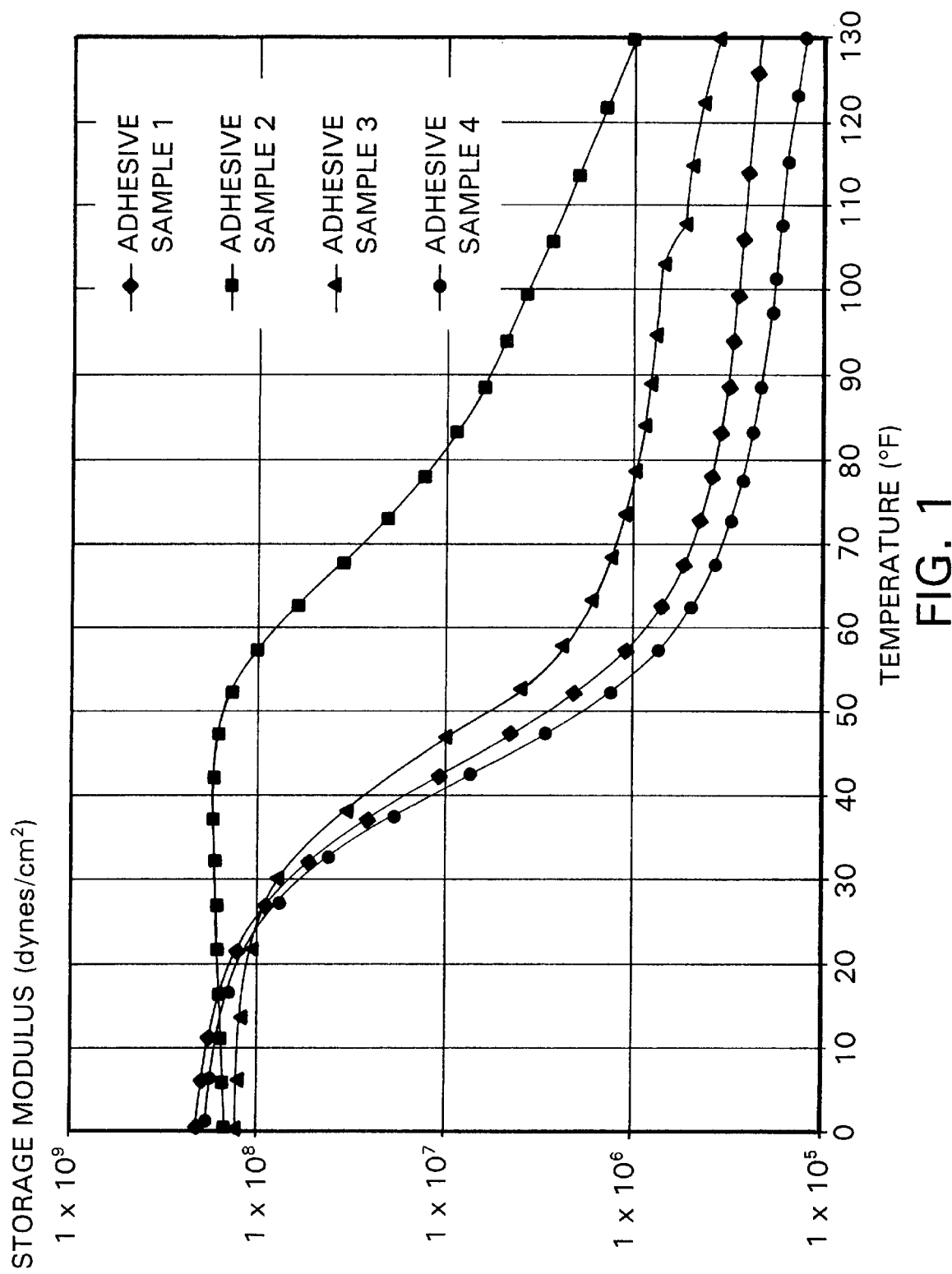
FIG. 1 is a graph of the storage modulus values of a variety of adhesive samples.

The present invention is directed to the use of an adhesive to prepare a disposable absorbent product such that the disposable absorbent product exhibits desirable aesthetic properties. In particular, it is desired that the adhesive not be visible through the outer sheets of the disposable absorbent product. In order to achieve such desirable aesthetic properties of a disposable absorbent product, it has been discovered as part of the research work that led to the present invention that the adhesive needs to exhibit specific rheological properties.

As used herein, the term "adhesive" is intended to mean a substance that is capable of bonding other substances together by surface attachment. Adhesives useful in the present invention may generally be of any known type, such as a thermoplastic hot-melt adhesive or a reactive adhesive. An example of a thermoplastic hot-melt adhesive includes a synthetic, olefin-based adhesive with a micro-crystalline wax, available from the National Starch and Chemical Company under the trade designation 70-4741. A description of compositions of hot-melt adhesives can be found, for example, in "CRC Elastomer Technology Handbook", edited by Nicholas P. Cheremisinoff (CRC Press, 1993), Chapter 24, incorporated herein by reference. Examples of reactive adhesives include crosslinked amine-epoxide compounds or moisture-cured polyurethanes. The chemistry of such reactive adhesives is known to those skilled in the art.

The adhesive according to the present invention is suited for use in disposable absorbent products, such as diapers, adult incontinent products, and bed pads; in catamenial devices, such as sanitary napkins, and tampons; and in other absorbent products, such as wipes, bibs, wound dressings, and surgical capes or drapes, which are used to absorb a liquid, such as water, saline, synthetic urine, and body liquids, such as urine, menses, and blood. Accordingly, in another aspect, the present invention relates to a disposable absorbent product comprising the adhesive as described herein.

In one embodiment of the present invention, a disposable absorbent product is provided, which disposable absorbent product comprises a liquid-permeable topsheet, a backsheet attached to the topsheet, an absorbent structure positioned between the topsheet and the backsheet, and an adhesive exhibiting the rheological properties described herein, wherein the disposable absorbent product exhibits desired aesthetic properties. The adhesive may be used to attach the topsheet to the backsheet. Alternatively, the adhesive may be used to adhere either the topsheet or the backsheet to other components of the disposable absorbent product, such as tissue layers, leg flaps, fastening ears, tapes, or tabs, or other components typically used to construct a disposable absorbent product that are well known to one skilled in the art.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films, sometimes referred to as breathable films.

In one embodiment of the present invention, the adhesive is contacted with a breathable film. In another embodiment of the present invention, the adhesive is contacted with a breathable film/nonwoven laminate. As used herein, a material, such as a film, will be considered to be "breathable" if such material exhibits a Water Vapor Transmission Rate of at least about 100 $g/m^2/24$ hours as determined according to the Test Method described below in connection with the examples.

A particularly desirable breathable film generally comprises two basic components, the first being a polyolefin polymer such as a linear low density polyethylene and the second being a filler. When the film is bonded to a nonwoven layer to form a film/nonwoven laminate, a third component, being a bonding or tackifying agent, may also be used. These components are mixed together, heated and then extruded into a film layer using any one of a variety of film-producing processes known to those of ordinary skill in the film art including casting and blowing. Other additives and ingredients may be added to the film layer provided they do not seriously interfere with the ability of the film to breath and, if desired, to thermally bond with a fibrous polyolefin nonwoven web. Generally, on a dry weight basis, based upon the total weight of the film, the film layer will include from about 10 to about 90 weight percent of a thermoplastic polyolefin polymer or polymers and from about 10 to about 90 weight percent filler.

Linear low density polyethylene has been found to work quite well as the polyolefin used to prepare the breathable film. However, it is believed that any predominately linear polyolefin polymer can be used with the present invention. As used herein, "linear low density polyethylene" is meant to include polymers of ethylene and higher alpha olefin comonomers such as $C_3$–$C_{12}$ and combinations thereof. By "predominately linear" it is meant that the main polymer chain is linear with less than approximately 5 long chain branches per 1000 ethylene units. Long chain branches would include carbon chains greater than $C_{12}$. For predominately linear polyolefin polymers that are nonelastic, short chain branching ($C_3$–$C_{12}$) due to comonomer inclusion will typically be limited to less than 20 short chains per 1000 ethylene units and 20 or greater for polymers which are elastomeric. Examples of predominately linear polyolefin polymers include, but are not limited to, linear polyolefins such as ethylene, propylene, 1-butene, 4-methyl-pentene, 1-hexane, 1-octene and higher olefins as well as copolymers of the foregoing. In addition, copolymers of ethylene and other olefins including pentene, hexane, heptene, octene, and decene would also be examples of predominately linear thermoplastic polymers.

In addition to a polyolefin polymer, the film layer also includes a filler. As used herein a "filler" is meant to include particulates and other forms of materials which can be added to the film polymer extrusion blend and which will not chemically interfere with or adversely affect the extruded film but which are able to be uniformly dispersed throughout the film. Generally the fillers will be in particulate form and usually will have somewhat of a spherical shape with average particle sizes in the range of about 0.1 to about 7 microns. Both organic and inorganic fillers are contemplated to be within the scope of the present invention provided that they do not interfere with the film formation process, the breathability of the resultant film or, if desired, its ability to thermally bond to a fibrous polyolefin nonwoven web. Examples of fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivatives, chitin and chitin derivatives.

If a bonding agent or tackifying agent is used, its purpose is to permit bonding of the film layer to a nonwoven layer. Generally, examples of bonding agents include, but are not limited to, polyamides, ethylene copolymers such as ethylene vinyl acetate, ethylene ethyl acrylate, ethylene acrylic acid, ethylene methyl acrylate and ethylene normal-butyl acrylate, wood rosin and its derivatives, hydrocarbon resins, polyterpene resins, atactic polypropylene and amorphous polypropylene. Also included are predominately amorphous ethylene propylene copolymers commonly known as ethylene-propylene rubber and a class of materials referred to as toughened polypropylene and olefinic thermoplastic polymers where ethylene-propylene rubber is mechanically dispersed or molecularly dispersed via in-reactor multistage polymerization in polypropylene or polypropylenelpolyethylene blends.

It should be understood that the foregoing list of bonding or tackifying agents is illustrative only and not meant to limit the scope of the present invention. Any bonding agent which: is blendable with the other film and/or fiber polymers; is capable of permitting the bonding of the film layer to a nonwoven layer at temperatures at least 5° C. lower than the melting temperature of the primary polyolefin polymer component of the film blend; and, is capable of creating a bond between the layers which requires at least a 5 gram load to separate the layers, is considered to be a bonding agent for purposes of the present invention. Generally the bonding agent will comprise from about 2 to about 20 percent of the total weight of the film. While weight percentages outside this range can be used, at higher percentages the breathability of the film becomes compromised which, for disposable absorbent products, is generally not desirable.

The breathable films may be formed using any one of the conventional processes known to those familiar with film formation. The polyolefin polymer, filler and, if used, the bonding agent are mixed in appropriate proportions given the ranges outlined above and then heated and extruded into a film. In order to provide uniform breathability as reflected by the water vapor transmission rate of the film, the filler should be uniformly dispersed throughout the polymer blend and, consequently, throughout the film itself. Generally, once the film is formed, it will have a weight per unit area of less than about 100 grams per square meter and after stretching and thinning its weight per unit area will be less than about 35 grams per square meter and more desirably less than about 18 grams per square meter.

The film used may be a blown film although other types of films are also considered to be within the scope of the present invention provided the forming technique is compatible with filled films. The film as initially formed is generally too thick and too noisy as it tends to make a "rattling" sound when shaken and the film does not yet have a sufficient degree of breathability as measured by its water vapor transmission rate. Consequently, the film is heated to a temperature at least about 5° C. less than the melting point of the polyolefin polymer used to prepare the film and then stretched to at least about 2.5 times its original length to thin the film and make it porous. More desirably, the temperature to which the film is heated during stretching is also less than the softening point of the bonding agent. For some bonding agents the softening point is given as a range. As a result, "heating below the softening point" would be at a temperature lower than the highest temperature given in the range.

An additional feature of the thinning process is the change in opacity of the film. As formed, the film is relatively transparent but after stretching, it often becomes opaque. In addition, while the film becomes oriented during the stretching process, it also becomes softer and it does not have the degree of "rattle" that it does prior to stretching. Taking all these factors into consideration, and the desire to have a water vapor transmission rate of at least 100 grams per square meter per 24 hours, the film should be thinned to such an extent that it has a weight per unit area of less than about 35 grams per square meter for disposable absorbent product applications and more desirably less than about 18 grams per square meter.

If used, a fibrous nonwoven layer may be made from polyolefin fibers such as polypropylene but other polyolefin fibers can be used too. Blends or mixtures of fibers are also possible including different polyolefin fibers and blends of polyolefin and non-polyolefin fibers such as polyethylene sheath/polypropylene core bicomponent fibers and polyester fibers. Natural fibers also may be included in the fibrous nonwoven web. Specific fiber types include single component fibers and multicomponent fibers such as side-by-side, sheath/core and islands-in-the-sea bicomponent fibers. The fibers may be straight or crimped, hollow or solid. They may have generally circular or non-circular cross-sections including bilobal, trilobal and "X" cross-sections. Fiber lengths may be short as with staple fibers or long as with spunbond and meltblown fibers. Fiber thicknesses will depend upon the desired properties. Narrow fibers will produce a softer nonwoven web while thicker fibers will provide more strength and resilience. Alternatively, blends of fiber diameters can be used. For disposable absorbent product applications, fiber diameters will typically range between about 1 and about 5 denier. For purposes of the present invention, a "polyolefin-based fibrous nonwoven web" and a "fibrous polyolefin nonwoven web" collectively refer to a fibrous nonwoven web wherein at least about 50% of the surface area of the fibers in the web constitute a polyolefin.

A variety of nonwoven web forming processes can be used with the present invention. Examples include, but are not limited to, air and wet laying, staple fiber carding and bonding, solution spinning, meltblowing and spunbonding processes. All of the foregoing processes are well known to those having ordinary skill in the art. Spunbonded polypropylene webs work particularly well with the present invention. Spunbond materials are made by extruding molten thermoplastic material as filaments through a plurality of capillaries in a spinneret with the diameter of the extruded filaments then being reduced by, for example, eductive drawing or other well known spunbonding mechanisms.

Once the fibrous nonwoven web layer has been formed it can be prebonded for added strength and integrity. Bond densities between about 100 and 300 bond points per square inch can be used with the specific density being dependent upon the size of the individual bond points.

To form a breathable, cloth-like film/nonwoven composite, the film layer and the fibrous polyolefin nonwoven layer are brought into contact with one another and then are thermally bonded together using a bonding means. Typically the film will have been extruded, stretched and thinned and then wound up on a roll prior to being incorporated into the composite. Alternatively, the film can be wound on a roll in an unstretched state and then stretched and thinned as it is fed into the process. As yet a further alternative, the film can be formed and stretched in line.

The fibrous nonwoven web also can be preformed and unwound from a supply roll into the bonding process. Alternatively, it too can be formed in line. If the film and nonwoven web are fed into the bonder at the same speed, a composite will be formed that will be relatively two-dimensional. Alternatively, the composite can be caused to retract thereby producing an undulating, thicker, more three-dimensional structure. One way of causing this retraction is to place one of the two layers under tension during the bonding process as by speeding up and/or braking one of the layers so that it is temporarily stretched or expanded. Once the bonding has been completed, the stretching or braking forces are removed and the composite retracts thereby causing the undulations. Another way is to use the stressed state of the oriented linear polyolefin molecules within the film layer. As a result of applying heat to the film layer, it will oftentimes want to retract. Consequently, if the composite is wound up on a take-up roll at a speed less than the speed of the composite at the bonder, the film will relax thereby causing undulations.

Thermal bonding of the two layers together can be accomplished by at least two methods. The first is using heat and pressure as with heated, patterned bonding rolls. Both rolls may be patterned or one may be patterned and the other may be smooth. One or both of the rolls may be heated or a secondary heat source may be used. If conditions dictate, one of the rolls may be cooled. In any event, the heat should be adjusted so that the bonding agent in the film becomes tacky to bond the two layers together while still maintaining the temperature at least about 5° C. cooler than the melting point of the primary polyolefin polymer in the film. By "primary" it is meant the polyolefin polymer having the highest weight percent of the total weight of the film if there is more than one polyolefin polymer in the film polymer blend.

Bond patterns and area may be varied depending upon the particular end-use. Suitable bond patterns can include point bonds, continuous lines, decorative patterns and combinations of the foregoing. Bond area will depend upon the degree of lamination desired. For disposable absorbent product applications, bonding should be sufficient to require at least a 5 gram load to delaminate the two layers.

The second method of bonding is ultrasonic bonding which also is well known to those having ordinary skill in the art. Here again the anvil roll can be designed with any of the bond patterns described above.

An absorbent structure is typically present in a disposable absorbent product in the form of a fibrous matrix comprising a hydrogel-forming polymeric material, commonly referred to as a superabsorbent material. A fibrous matrix may take the form of, for example, a batt of comminuted wood pulp fluff, a tissue layer, a hydroentangled pulp sheet, or a mechanically softened pulp sheet. Suitably, the fibrous matrix is formed so as to constrain or entrap the hydrogel-forming polymeric material within, or onto, its structure. The hydrogel-forming polymeric material may be incorporated into or onto the fibrous matrix either during or after the formation of the general form of the fibrous matrix. A fibrous matrix useful in the present invention may be formed by an air-laying process or a wet-laid process, or by essentially any other process known to those skilled in the art for forming a fibrous matrix.

Disposable absorbent products and structures according to all aspects of the present invention are generally subjected, during use, to multiple insults of a body liquid. Accordingly, the disposable absorbent products are desirably capable of absorbing multiple insults of body liquids in quantities to which the disposable absorbent products will be exposed during use. The insults are generally separated from one another by a period of time.

It has been discovered as part of the present research work that adhesive staining of frontsheets or backsheets, and particularly microporous polyolefin films such as breathable films, is generally a result of two independent mechanisms. First, localized heat degradation occurring during the preparation of a disposable absorbent product can cause a frontsheet or backsheet to burn through or degrade, resulting in the appearance of dark adhesive swirl patterns due to the poor light reflecting qualities of the adhesive in comparison to the frontsheet or backsheet substrate. A second mechanism results from a change in light-reflecting properties at the adhesive-substrate interface, causing more light to refract through the substrate instead of reflecting off the surface of the frontsheet or backsheet substrate. Materials containing whitening pigments, such as titanium dioxide ($TiO_2$), generally appear white as a result of the high refractive index of the pigment in comparison to the material to which the pigment has been added.

Microporous polyolefin films that comprise an inorganic filler but which don't comprise a pigment in their formulation may also appear white as a result of the air gaps within and at the surface of the microporous polyolefin films. As an example, a polyethylene film comprising calcium carbonate particles as an inorganic filler generally appears translucent when the polyethylene film is unstretched because the calcium carbonate and the polyethylene exhibit similar refractive indices (each of about 1.5). When the polyethylene film is stretched to form a microporous film, air gaps are formed by the edges of the calcium carbonate within the film and at the film surface. Such air gaps within the film generally provide a phase with a refractive index that is sufficiently different from the polyethylene film to result in the reflection of light, and, at the film surface cause a general roughening, both of which give the microporous film a generally white appearance. When an adhesive is applied to a substrate such as a microporous polyolefin film, such application of the adhesive may affect the aesthetic appearance of the microporous polyolefin film.

Light generally refracts or bends when passing through two materials with different refractive indexes. Snell's law relates the refractive index (n) of two materials to the sine of the angle of incidence (i), divided by that of the angle of refraction (r) as shown in the following equation:

$$\frac{n_r}{n_i} = \frac{\sin(i)}{\sin(r)}$$

When light passes from a material with a higher refractive index to a material with a lower refractive index, the incident angle may become so large that no light is refracted into the less dense medium. This takes place when the angle of refraction becomes 90°, and the above equation becomes:

$$\sin(i) = \frac{n_r}{n_i}$$

Angle (i) is then referred to as the critical angle, C, and may be expressed in terms of the refractive index of both the adhesive ($n_{Adhesive}$) and the film substrate ($n_{Film}$), as shown in the following equation:

$$\sin(C) = \frac{n_{Adhesives}}{n_{Film}}$$

Total reflection results when the critical angle is exceeded, resulting in a white appearance of the film substrate. Light is refracted through the film substrate when striking the film substrate-adhesive interface at angles less than the critical angle, resulting in the visibility of adhesive application patterns. Since the refractive index of both the adhesive and film substrate will generally be similar, the critical angle is relatively large, and the majority of incoming light is refracted through the film substrate, allowing the film substrate to appear translucent.

If the refractive index of the film substrate is increased, the sine of the critical angle would decrease, allowing the critical angle to also decrease. In this case, the angle of a majority of incoming light is greater than the critical angle, resulting in reflection of a majority of incoming light. Unfortunately, film substrates with such a high refractive index are generally not available or, if available, would generally not be economical to use in most disposable absorbent products. The addition of pigments to the film formulation would also increase the reflection of light, but would generally increase the cost and complexity of processing such a film formulation.

As a result of the present research work, a solution to the problem of adhesive staining was discovered by applying basic fundamentals of light reflection and refraction to modify the interface between the adhesive and a sheet substrate, such as a microporous polyolefin film, in a way that increases light reflection and reduces light refraction. In particular, it has been discovered that adhesive staining of a microporous polyolefin film is generally caused by a substantially intimate contact of the microporous polyolefin film with the adhesive, resulting for example by the wetting out of the adhesive onto the microporous polyolefin film. In such a situation, relatively few or no air gaps will exist between the interface of the microporous polyolefin film with the adhesive. The absence of air gaps at the interface of the microporous polyolefin film with the adhesive allows for the refraction of more light through the microporous polyolefin film and less back to an observer. The interface of a microporous polyolefin film with an adhesive, and the existence or absence of air gaps, may generally be determined by any of several analytical methods, such as with scanning electron microscopy.

In contrast, it has been discovered that adhesive staining of a microporous polyolefin film may generally be avoided by using an adhesive that does not achieve a substantially intimate contact with the microporous polyolefin film substrate. By not achieving a substantially intimate contact between an adhesive and a microporous polyolefin film substrate, air gaps generally exist between bonding points of the adhesive to the microporous polyolefin film substrate. Since the refractive index of air (about 1.0) is less than that of a typical microporous polyolefin film substrate (about 1.5), the critical angle of such an interface is decreased, resulting in more reflection of light. In such a situation, the amount of adhesive staining will be substantially reduced or even eliminated, since a sufficient amount of light is reflected from the surface of the microporous polyolefin film substrate instead of refracted through the microporous polyolefin film substrate. Therefore, in order for an adhesive to substantially resist the optical staining of a substrate, such as a microporous polyolefin film, the adhesive must exhibit controlled wet-out properties that limit the intimate contact between the adhesive and the substrate. For this to be possible, the adhesive must be highly resistant to flow in the temperature range in which disposable absorbent products are commonly stored or used, which is typically in the temperature range of between about 0° F. to about 130° F. (about −18° C. to about 54° C.). Such a resistance to flow may be quantified by the adhesive exhibiting a storage modulus (G') that is sufficiently high to substantially resist flow within the temperature range of between about 0° F. to about 130° F. (about −18° C. to about 54° C.).

The storage modulus of a material is a coefficient of elasticity representing the ratio of stress to strain as the material is deformed under a dynamic load. The storage modulus of a material generally is a measure of the softness or stiffness of the material. The storage modulus of a material may be determined according to test methods well known to those skilled in the art. As reported or used herein in the present specification, examples, and claims, the Storage Modulus value for an adhesive sample is reported as measured according to ASTM Test Method D 4440 - 95a, "Standard Practice for Rheological Measurement of Polymer Melts Using Dynamic Mechanical Procedures", hereby incorporated herein in its entirety.

In one embodiment of the present invention, it is desired that the adhesive useful in the present invention exhibit a Storage Modulus value, at about 80° F. (about 27° C.), that is beneficially greater than about $3 \times 10^6$ dynes per square centimeter, more beneficially greater than about $5 \times 10^6$ dynes per square centimeter, suitably greater than about $7 \times 10^6$ dynes per square centimeter, more suitably greater than about $1 \times 10^7$ dynes per square centimeter, and up to about $1 \times 10^{10}$ dynes per square centimeter.

In another embodiment of the present invention, it is desired that the adhesive exhibit a Storage Modulus value, across the temperature range of about 70° F. to about 90° F. (about 21° C. to about 32° C.), that is beneficially greater than about $3 \times 10^6$ dynes per square centimeter, more beneficially greater than about $5 \times 10^6$ dynes per square centimeter, suitably greater than about $7 \times 10^6$ dynes per square centimeter, more suitably greater than about $1 \times 10^7$ dynes per square centimeter, and up to about $1 \times 10^{10}$ dynes per square centimeter.

In another embodiment of the present invention, it is desired that the adhesive exhibit a Storage Modulus value, across the temperature range of about 0° F. to about 130° F. (about −18° C. to about 54° C.), that is beneficially greater than about $1 \times 10^6$ dynes per square centimeter, more beneficially greater than about $3 \times 10^6$ dynes per square centimeter, even more beneficially greater than about $5 \times 10^6$ dynes per square centimeter suitably greater than about $7 \times 10^6$ dynes per square centimeter, more suitably greater than about $1 \times 10^7$ dynes per square centimeter, and up to about $1 \times 10^{10}$ dynes per square centimeter.

It is also desired that the adhesive useful in the present invention exhibit a melting or softening temperature within a range that is typically encountered in most process applications for preparing or manufacturing disposable absorbent products. In general, it is desired that the adhesive exhibit a melting or softening temperature that is low enough to prevent thermal degradation of a substrate to which the adhesive is being applied. As such, it is generally desired that the Softening Temperature value of an adhesive useful in the present invention beneficially be between about 50° F. to about 350° F., more beneficially be between about 75° F. to about 325° F., and suitably be between about 100° F. to about 300° F. As reported or used herein in the present specification, examples, and claims, the Softening Temperature value for an adhesive sample is reported as measured according to ASTM Test Method D 36 - 86 (Reapproved 1989), "Standard Test Method for Softening Point of Bitumen (Ring-and-Ball Apparatus)", hereby incorporated herein in its entirety.

It is generally desired that the adhesive be present in a disposable absorbent product in an amount effective to result in the disposable absorbent product exhibiting desired properties. If the adhesive is present in a disposable absorbent product in too small of an amount, the disposable absorbent product will generally exhibit poor integrity or tensile strength. In contrast, if the adhesive is present in a disposable absorbent product in too large of an amount, the disposable absorbent product may more readily exhibit adhesive staining, more readily exhibit heat degradation of a topsheet or backsheet substrate, or be more expensive to manufacture due to the use of an amount of the adhesive that is greater than is really needed.

In one embodiment of the present invention, the adhesive will be applied to a substrate, such as a breathable film, in an amount that is beneficially between about 0.5 gram to about 10 grams, more beneficially between about 1 gram to about 8 grams, and suitably between about 2 grams to about 6 grams per square meter of applied surface area of the adhesive.

It is desired that when the adhesive is contacted with a substrate, such as a breathable film, that the substrate not exhibit an undesirable amount of adhesive staining. In one embodiment of the present invention, it is generally desired that a substrate, such as a breathable film, when contacted with an adhesive of the present invention, exhibits an Adhesive Staining value, at a temperature of about 73° F. (about 23° C.) that is beneficially less than about 175, more beneficially less than about 100, suitably less than about 50, more suitably less than about 25, and even more suitably less than about 10.

In another embodiment of the present invention, it is generally desired that a substrate, such as a breathable film, when contacted with an adhesive of the present invention, exhibits an Adhesive Staining value, at a temperature of about 130° F. (about 54° C.) that is beneficially less than about 500, more beneficially less than about 250, suitably less than about 175, more suitably less than about 100, and even more suitably less than about 50. As reported or used herein in the present specification, examples, and claims, the Adhesive Staining value for a sample is the total area under the intensity profile exhibited by the substrate and adhesive sample and as determined by the Test Method described below in connection with the examples.

Test Methods

Adhesive Staining

An eight inch long by one inch wide strip of a substrate sample, with or without an adhesive applied to it, was prepared or obtained, for example, from the end seal of a prepared diaper wherein the eight inch length is in the cross machine direction of the prepared diaper. The sample was stored for 30 days at a specified temperature, such as at about 73° F. (about 23° C.) or at about 130° F. (about 54° C.). The substrate sample was placed over a black background. A digital image of the sample was acquired using a flat bed scanner, available from the Hewlett-Packard Company, of Palo Alto, Calif., under the designation ScanJet 4C flat bed scanner, in combination with a computer with suitable software, available from Hewlett-Packard Company, of Palo Alto, Calif., under the designation DeskScan II software, version 2.0. The digital image was run through a filter software program, available from Corel Corporation, of Orem, Utah, under the designation Photo-Paint software, version 5.00.F4, where the brightness, contrast, and intensity were adjusted (using settings of −68, 100, and 41 respectively) to amplify the visibility of any adhesive staining. An intensity profile was generated with the use of an image analysis software program, available from Keystone Automation Inc., of Lake Elmo, Minn., under the designation Eye Image Calculator software, version 2.0 for Windows95™. The intensity (whiteness) of a sample was measured over a line drawn through the sample in the cross direction. The line is 445 pixels in length, and the maximum pixel intensity (saturated white) is 255 and the minimum pixel intensity (saturated black) is 0. As used herein, pixel intensity is a unitless number. The magnitude of adhesive staining is quantified by subtracting the intensity of each pixel from 255. For example, a pure white pixel will have a value of 0 and a pure black pixel will have a value of 255. The total area under the intensity profile (magnitude of staining) is obtained by summing the values for all pixels in the line. A pure white line (no staining) will have a total value of 0 and a pure black line (complete staining) will have a value of 255×455=116025. Thus, lower values of the total area under the intensity profile and the average intensity across the sample represent lower adhesive staining. As reported or used herein in the present specification, examples, and claims, the Adhesive Staining value for a sample is the total area under the intensity profile exhibited by the sample and as determined by this test method.

Water Vapor Transmission Rate

The Water Vapor Transmission Rate value, in grams of water vapor transmitted per square meter of material per 24 hours, for a sample material was calculated in accordance with ASTM Standard E96-80. Circular samples measuring three inches in diameter were cut from each of the test materials and a control which was a piece of CELGUARD™ 2500 film from Hoechst Celanese Corporation of Sommerville, N.J. CELGUARD™ 2500 film is a microporous polypropylene film. Five samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (about 32° C.) for about one hour to equilibrate. The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans were removed from the oven, weighed and immediately returned to the oven. After 24 hours, the pans were removed from the oven and weighed again. The preliminary test Water Vapor Transmission Rate (WVRT) value for a sample was calculated as follows:

Test WVRT=(grams weight loss over 24 hours)×315.5 g/m$^2$/24 hours

The relative humidity within the oven was not specifically controlled.

Under predetermined set conditions of about 100° F. (about 32° C.), an ambient relative humidity (generally between about 30 to about 70 percent relative humidity), the WVRT for the CELGUARD™ 2500 film was determined to be about 5000 grams per square meter of film for 24 hours. Accordingly, the control sample was run with each test and the preliminary test WVRT values were corrected to set conditions using the following equation:

WVRT=(test WVRT/control WVRT)×5000 g/m$^2$/24 hours

EXAMPLES

Example 1

Various adhesives were evaluated for Storage Modulus values across a range of temperatures.

Adhesive Sample 1 was obtained from National Starch and Chemical Company, of Bridgewater, N.J., under the designation 34-5610 adhesive. Adhesive Sample 1 is a rubber-based hot melt adhesive which is a clear ivory solid at room temperatures, comprises about 100 weight percent solids, has a softening point of about 163° F. (about 73° C.), has a density of about 8.4 pounds per gallon, and exhibits a viscosity ranging from about 2,175 centipoise (mPa.s) at about 350° F. (about 177° C.) to about 205,000 centipoise (mPa.s) at about 200° F. (about 93° C.). The Storage Modulus values for Adhesive Sample 1 are shown in Table 1.

Adhesive Sample 2 was obtained from National Starch and Chemical Company, of Bridgewater, N.J., under the designation 70-4741 adhesive. Adhesive Sample 2 is an olefin-based hot melt adhesive with a micro-crystalline wax included to enhance processability. The Storage Modulus values for Adhesive Sample 2 are shown in Table 2.

Adhesive Sample 3 was obtained from H. B. Fuller Company, of St. Paul, Minn., under the designation HL-1500-X adhesive. Adhesive Sample 3 is a hot melt adhesive comprising between 10 to 30 weight percent of hydrogen oil, has a molten Gardner color of about 2, has a softening point (according to ASTM Test Method D3461) of about 178.5° F. (about 81° C.), and exhibits a viscosity ranging from about 325 centipoise (mPa.s) at about 325° F. (about 163° C.) to about 6,375 centipoise (mPa.s) at about 200° F. (about 93° C.). The Storage Modulus values for Adhesive Sample 3 are shown in Table 3.

Adhesive Sample 4 was obtained from National Starch and Chemical Company, of Bridgewater, N.J., under the designation 34-5616 adhesive. Adhesive Sample 4 is a rubber-based hot melt adhesive. The Storage Modulus values for Adhesive Sample 4 are shown in Table 4.

The Storage Modulus values for Adhesive Samples 1–4 are visually summarized in FIG. 1.

TABLE 1

Storage Modulus values for Adhesive Sample 1*

| Temperature (° F.) | Storage Modulus (dynes/square centimeter) |
| --- | --- |
| 1 | 2.11 × 10$^8$ |
| 6 | 1.98 × 10$^8$ |
| 11 | 1.81 × 10$^8$ |
| 16 | 1.59 × 10$^8$ |
| 22 | 1.29 × 10$^8$ |
| 27 | 9.08 × 10$^7$ |
| 32 | 5.31 × 10$^7$ |
| 37 | 2.56 × 10$^7$ |
| 42 | 1.08 × 10$^7$ |
| 47 | 4.49 × 10$^6$ |
| 52 | 2.03 × 10$^6$ |
| 57 | 1.09 × 10$^6$ |
| 63 | 7.10 × 10$^5$ |
| 68 | 5.35 × 10$^5$ |
| 73 | 4.37 × 10$^5$ |
| 78 | 3.76 × 10$^5$ |
| 83 | 3.37 × 10$^5$ |
| 89 | 3.09 × 10$^5$ |
| 94 | 2.90 × 10$^5$ |
| 99 | 2.75 × 10$^5$ |
| 106 | 2.61 × 10$^5$ |
| 114 | 2.45 × 10$^5$ |
| 126 | 2.18 × 10$^5$ |
| 132 | 2.06 × 10$^5$ |

*Not an example of the present invention

TABLE 2

Storage Modulus values for Adhesive Sample 2

| Temperature (° F.) | Storage Modulus (dynes/square centimeter) |
| --- | --- |
| 1 | 1.5 × 10$^8$ |
| 6 | 1.54 × 10$^8$ |
| 11 | 1.57 × 10$^8$ |
| 16 | 1.61 × 10$^8$ |
| 22 | 1.64 × 10$^8$ |
| 27 | 1.66 × 10$^8$ |
| 32 | 1.69 × 10$^8$ |
| 37 | 1.73 × 10$^8$ |
| 42 | 1.74 × 10$^8$ |
| 47 | 1.64 × 10$^8$ |
| 52 | 1.39 × 10$^8$ |
| 57 | 1.02 × 10$^8$ |
| 63 | 6.17 × 10$^7$ |
| 68 | 3.56 × 10$^7$ |
| 73 | 2.04 × 10$^7$ |
| 78 | 1.30 × 10$^7$ |
| 83 | 8.74 × 10$^6$ |
| 89 | 6.28 × 10$^6$ |
| 94 | 4.77 × 10$^6$ |
| 99 | 3.76 × 10$^6$ |
| 106 | 2.75 × 10$^6$ |
| 114 | 1.99 × 10$^6$ |
| 122 | 1.42 × 10$^6$ |
| 130 | 1.02 × 10$^6$ |

TABLE 3

Storage Modulus values for Adhesive Sample 3*

| Temperature (° F.) | Storage Modulus (dynes/square centimeter) |
| --- | --- |
| 0 | 1.32 × 10$^8$ |
| 6 | 1.28 × 10$^8$ |
| 14 | 1.23 × 10$^8$ |
| 22 | 1.10 × 10$^8$ |

TABLE 3-continued

Storage Modulus values for Adhesive Sample 3*

| Temperature (° F.) | Storage Modulus (dynes/square centimeter) |
|---|---|
| 30 | $7.94 \times 10^7$ |
| 38 | $3.40 \times 10^7$ |
| 47 | $9.74 \times 10^6$ |
| 53 | $3.98 \times 10^6$ |
| 58 | $3.98 \times 10^6$ |
| 63 | $1.68 \times 10^6$ |
| 68 | $1.32 \times 10^6$ |
| 74 | $1.10 \times 10^8$ |
| 79 | $9.64 \times 10^5$ |
| 84 | $8.77 \times 10^5$ |
| 89 | $8.12 \times 10^5$ |
| 95 | $7.61 \times 10^5$ |
| 103 | $6.61 \times 10^5$ |
| 108 | $5.39 \times 10^5$ |
| 115 | $4.94 \times 10^5$ |
| 123 | $4.35 \times 10^5$ |
| 131 | $3.42 \times 10^5$ |

*Not an example of the present invention

TABLE 4

Storage Modulus values for Adhesive Sample 4*

| Temperature (° F.) | Storage Modulus (dynes/square centimeter) |
|---|---|
| 1 | $1.90 \times 10^8$ |
| 7 | $1.80 \times 10^8$ |
| 12 | $1.65 \times 10^8$ |
| 17 | $1.44 \times 10^8$ |
| 22 | $1.15 \times 10^8$ |
| 27 | $7.77 \times 10^7$ |
| 33 | $4.22 \times 10^7$ |
| 38 | $1.86 \times 10^7$ |
| 43 | $7.29 \times 10^8$ |
| 47 | $2.90 \times 10^8$ |
| 52 | $1.31 \times 10^8$ |
| 57 | $7.36 \times 10^5$ |
| 63 | $4.88 \times 10^5$ |
| 68 | $3.70 \times 10^5$ |
| 73 | $3.01 \times 10^5$ |
| 78 | $2.60 \times 10^5$ |
| 83 | $2.31 \times 10^5$ |
| 89 | $2.09 \times 10^5$ |
| 97 | $1.82 \times 10^5$ |
| 101 | $1.77 \times 10^5$ |
| 108 | $1.65 \times 10^5$ |
| 115 | $1.51 \times 10^5$ |
| 123 | $1.37 \times 10^5$ |
| 131 | $1.20 \times 10^5$ |

*Not an example of the present invention

Example 2

A control diaper was prepared using Adhesive Sample 1, obtained from National Starch and Chemical Company, of Bridgewater, N.J., under the designation 34-5610 adhesive. This control diaper exhibited considerable adhesive staining through the breathable outer cover after preparation and viewing at room temperature [about 72° F. (about 22° C.)].

A diaper was prepared using Adhesive Sample 2, obtained from National Starch and Chemical Company, of Bridgewater, N.J., under the designation 70-4741 adhesive. This diaper did not exhibit any visible adhesive staining through the breathable outer cover, even after six days of storage at about 130° F. (about 54° C.).

Example 3

A control diaper was prepared using Adhesive Sample 4, obtained from National Starch and Chemical Company, of Bridgewater, N.J., under the designation 34-5616 adhesive. This control diaper was evaluated for adhesive staining using the Test Method described herein. This control diaper exhibited an Adhesive Staining value of about 488 at a storage temperature of about 73° F. (about 23° C.) and an Adhesive Staining value of about 5563 at a storage temperature of about 130° F. (about 54° C.).

A diaper was prepared using Adhesive Sample 2, obtained from National Starch and Chemical Company, of Bridgewater, N.J., under the designation 70-4741 adhesive. This diaper was evaluated for adhesive staining using the Test Method described herein. This diaper exhibited an Adhesive Staining value of about 7 at a storage temperature of about 73° F. (about 23° C.) and an Adhesive Staining value of about 421 at a storage temperature of about 130° F. (about 54° C.).

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A disposable absorbent product comprising a liquid-permeable topsheet, a backsheet attached to the topsheet, an absorbent structure positioned between the topsheet and the backsheet, and an adhesive contacting the backsheet, wherein:

a. the backsheet comprises a film wherein the film comprises, on a dry weight basis, based upon the total weight of the film, from about 10 to about 90 weight percent of a thermoplastic polyolefin polymer and from about 10 to about 90 weight percent of a filler, wherein the film exhibits a Water Vapor Transmission Rate of at least about 100 g/m²/24 hours and a weight per unit area of less than about 100 grams per square meter; and b. the adhesive exhibits a Storage Modulus value, across the temperature range of about 0° F. to about 130° F., that is greater than about $1 \times 10^6$ dynes per square centimeter and a Softening Temperature value between about 50° F. to about 350° F.

2. The disposable absorbent product of claim 1 wherein the adhesive exhibits a Storage Modulus value, across the temperature range of about 0° F. to about 130° F., that is greater than about $3 \times 10^6$ dynes per square centimeter.

3. The disposable absorbent product of claim 2 wherein the adhesive exhibits a Storage Modulus value, across the temperature range of about 0° F. to about 130° F., that is greater than about $5 \times 10^6$ dynes per square centimeter.

4. The disposable absorbent product of claim 1 wherein the adhesive exhibits a Storage Modulus value, across the temperature range of about 0° F. to about 130° F., that is greater than about $7 \times 10^6$ dynes per square centimeter.

5. The disposable absorbent product of claim 1 wherein the adhesive is a hot melt adhesive.

6. The disposable absorbent product of claim 1 wherein the adhesive is an olefin-based, hot melt adhesive.

7. The disposable absorbent product of claim 1 wherein the backsheet exhibits an Adhesive Staining value, after storage for 30 days at a temperature of about 73° F., that is less than about 175.

8. The disposable absorbent product of claim 1 wherein the backsheet exhibits an Adhesive Staining value, after storage for 30 days at a temperature of about 73° F., that is less than about 100.

9. The disposable absorbent product of claim 1 wherein the thermoplastic polyolefin polymer is selected from the group consisting of polyethylene and polypropylene.

10. The disposable absorbent product of claim 1 wherein the film exhibits a weight per unit area of less than about 35 grams per square meter.

11. The disposable absorbent product of claim 1 wherein the filler is selected from the group consisting of calcium carbonate, clay, silica, alumina, barium sulfate, sodium carbonate, talc, magnesium sulfate, titanium dioxide, zeolites, aluminum sulfate, cellulose powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, chitin and chitin derivatives.

12. The disposable absorbent product of claim 11 wherein the filler is calcium carbonate.

13. The disposable absorbent product of claim 1 wherein the adhesive is a hot melt adhesive, the thermoplastic polyolefin polymer is selected from the group consisting of polyethylene and polypropylene, the filler is calcium carbonate, and the film exhibits a weight per unit area of less than about 35 grams per square meter.

14. The disposable absorbent product of claim 13 wherein the backsheet exhibits an Adhesive Staining value, after storage for 30 days at a temperature of about 73° F., that is less than about 175.

* * * * *